United States Patent [19]
Valjukas et al.

[11] 4,134,885
[45] Jan. 16, 1979

[54] ANTI-ANTIHEMOCYTIC SERUM AND A METHOD FOR THE PREPARATION THEREOF

[76] Inventors: Juozas B. Valjukas, ulitsa Antakalne, 65, kv. 50; Marionas A. Babyanskas, ulitsa Melnikaites, 8, kv. 30; Pyatras A. Zayanchkauskas, ulitsa Cherno, 10, kv. 54; Yanina I. Zhukauskene, ulitsa Arkhitektu, 168, kv. 18, all of Vilnjus, U.S.S.R.

[21] Appl. No.: 865,489
[22] Filed: Dec. 29, 1977
[51] Int. Cl.$^2$ ............................................... A23J 1/06
[52] U.S. Cl. ................................. 260/112 B; 424/101
[58] Field of Search ...................... 260/112 B; 424/101

[56] References Cited
PUBLICATIONS
Olefir, Chemical Abstracts, vol. 79:74,595a (1973).

Primary Examiner—Walter C. Danison
Attorney, Agent, or Firm—Robert E. Burns; Emmanuel J. Lobato; Bruce L. Adams

[57] ABSTRACT

The anti-antihemocytic serum comprises water-soluble proteins in a physiological solution isolated from cells of the bodies of insects immunized by a single injection in a dose of 0.25 $\mu$l to 2.0 $\mu$l for every insect with the anti-hemocytic serum produced from the plasma of the blood of an animal immunized with a suspension of hemocytes from cells of the bodies of the given species of insects. The titre of hemocytoagglutinins of the anti-antihemocytic serum is 1:256 to 1:1024. The method for the preparation of anti-antihemocytic serum resides in immunizing the given species of insects with anti-hemocytic serum, produced from the plasma of the blood of an animal immunized with a suspension of hemocytes from cells of the bodies of insects, by means of a single injection in a dose of 0.25 to 2.0 $\mu$l for every insect, removing the hemolymph and the alimentary tract from insects in 24 hours, homogenizing the remaining cells of the bodies of insects and diluting them with a physiological solution, isolating proteins from cells of the bodies of insects by breaking the integrity of cells, and isolating the fluid from the resultant mixture separating it from the indissoluble portion of cells of the bodies of insects, obtaining the target product.

2 Claims, No Drawings

ANTI-ANTIHEMOCYTIC SERUM AND A METHOD FOR THE PREPARATION THEREOF

The present invention relates to agriculture, and more particularly to a new anti-antihemocytic serum and a method for the preparation thereof. The proposed new serum finds application in controlling pests such as cabbage white butterfly, bee moth, Colorado potato beetle, and others.

There are known in the art various biological preparations for protection of plants from pests, namely, such preparations as agritrol, bactan, biospore 2802, and others.

When these bacterial preparations are used insect pests soon acquire immunity to them, and with prolonged application they do not produce a positive effect.

The proposed anti-antihemocytic serum is new and has not been described in literature.

According to the invention the anti-antihemocytic serum comprises water-soluble proteins in a physiological solution isolated from cells of the bodies of insects immunized by a single injection of 0.25 μl to 2.0 μl for every insect of anti-hemocytic serum prepared from the blood plasma of an animal immunized with a suspension of hemocytes from cells of the bodies of the given species of insects; the titre of hemocytoagglutinins of the anti-antihemocytic serum is 1:256 to 1:1024.

As distinct from the known biological means of pest control, the proposed serum suppresses the immunologic reactivity of insect pests, and improves the pathogenic properties of bacteria parasitizing on these insects. The proposed serum is harmless to the environment.

The proposed serum can be used for controlling any species of insect pests, and for every species of insects a serum is used which has been prepared on the basis of cells of the body of the insect of the respective species.

According to the invention, the method for the preparation of the proposed serum resides in immunizing the given species of insects with anti-hemocytic serum, prepared from the blood plasma of an animal immunized with a suspension of hemocytes from cells of the body of the insect, by a single injection in a dose of 0.25 to 2.0 μl for every insect, removing the hemolymph in 24 hours and the alimentary tract, homogenizing the remaining cells of the bodies of insects and diluting with a physiological solution, isolating proteins from cells of the bodies of insects by breaking the integrity of cells, and isolating the fluid from the resultant mixture separating it from the indissoluble portion of cells of the bodies of insects, thus obtaining the target product.

The proposed method is effected in the following manner.

The starting material used is anti-hemocytic serum. The anti-hemocytic serum is obtained by removing the alimentary tract and the hemolymph from insects, the remaining cells of the bodies of insects are then preserved and homogenized to form a suspension of hemocytes. The resultant mixture is washed off from the preservative prior to immunization and animals are then immunized 4 times with intervals of 5 days, by injecting a 50% suspension of hemocytes in an amount of 0.07 ml per 100 g of the weight of an animal. After immunization the whole blood of animals is removed, the blood plasma is isolated and inactivated. The anti-hemocytic serum produced is administered into insects by a single injection in a dose of 0.25 to 2 μl for every insect. The hemolymph and the alimentary tract of insects are removed 24 hours after the injection. The bodies of insects are then washed with a physiological solution. To extract water-soluble proteins the bodies of insects are homogenized and diluted with a physiological solution, preferably in a ratio of 1:1.

To destroy the cells the resultant mass is frozen and thawed many times.

Then the resultant mixture is centrifuged. The liquid over the precipitate is poured off. The anti-antihemocytic serum is obtained which is kept at a temperature of 20±2° C. below zero. The titre of hemocytoagglutinins of the anti-antihemocytic serum is 1:256 to 1:1024. The proposed anti-antihemocytic serum was tested on various species of insects.

The serum was applied by spraying. The test results showed a high activity of the proposed serum. The effectiveness of destruction of insects was from 70 to 100% depending on the dose of the serum applied to insects.

The proposed serum can also be used in combination with entomopathogenic bacteria.

For a better understanding of the present invention the following examples illustrating the method for the preparation of the anti-antihemocytic serum and methods for testing its activity are presented below.

Example 1. Caterpillars of *Galleria mellonella L* numbering 2,000 in the period of their development (V–VI nistars) are disinfected with ehtyl alcohol and left for 5 to 6 hours to clean the alimentary tract. Live caterpillars are then placed in a preservative consisting of the following components, in grams: sodium citrate 3.5; glucose 2.0; cloramphenicol 0.015; distilled water up to 100. The preservative is taken in an amount of 1 ml for 10 caterpillars. Then one segment is removed from the front and one from the rear portion of the bodies of caterpillars. The alimentary tract is removed to prevent the action of enzymes. The remaining bodies of caterpillars are ground and together with said preservative placed for 7 to 10 minutes in a magnetic mixer for complete separation of the hemolymph. The resultant homogenate is filtered and centrifuged 6 to 7 times for 15 minutes at 1,000 r.p.m.

The centrifugate is left for 30 minutes at room temperature and the upper fat-like layer thus formed is removed with a cottonwool wad. The plasma of the hemolymph is poured off, and the cells are filled with a solution consisting of 0.24 M of saccharose, 0.004 M of etylene diaminetetra-acetic acid, 0.01 M of sodium phosphate per 1,000 ml of distilled water, pH of 7.0, and glycerin in a weight ratio of 1:2:1 respectively. The resultant suspension of hemocytes is kept at a temperature of −20±2° C. Prior to immunization the preservative is washed off from it with a physiological solution. Thereafter 12 white rats weighing 300 g each are immunized 4 times with intervals of 5 days. Each time 0.2 ml of a 50% suspension of hemocytes is injected. The first immunization is done subcutaneously and 0.2 ml of a 50% suspension of hemocytes is injected in every rat. The subsequent immunizations are done intramuscularly by injecting 0.2 ml of a 50% suspension in mixture with 16,666 units of penicillin to prevent possible infection. Seven days after the last immunization the rats are dehematized. The separated blood is placed in glass cylinders and left at room temperature for 24 hours. The settled plasma is poured off and inactivated at 56° C. for 30 minutes. There is obtained 150 ml of anti-hemocytic serum.

The resultant anti-hemocytic serum is administered into caterpillars of *Galleria mellonella L* (5,000 in number) during the period of their development (V–VI nistars) by a single injection in a dose of 0.25 μl. The hemolymph and the alimentary tract are removed from caterpillars 24 hours after the injection. The bodies of caterpillars are then washed with a physiological solution, homogenized and diluted with a physiological solution in a ratio of 1:1. The resultant mass is frozen and thawed many times to break the integrity of cells. Then this mixture is centrifuged for 15 minutes at 8,000 r.p.m., the fluid over the precipitate is poured off and 125 ml of the anti-antihemocytic serum is obtained.

The anti-antihemocytic serum was tested on caterpillars of *Galleria mellonella L* during the period of their development (II–IV and V–VI nistars). Caterpillars were sprayed with the anti-antihemocytic serum in a dose of 0.25 to 2.5 μl for every caterpillar.

At the same time the action of the anti-antihemocytic serum was tested in combination with entomophatogenic bacteria *Bac.thuringiensis cereus var. galleriae.*

The dose of the anti-antihemocytic serum was 0.25 μl for every caterpillar, and *Bac.thuringiensis cereus var. galleriae* were used in the form of a 0.1% water suspension.

The following effects were determined:

(1) the effect of the anti-antihemocytic serum on the immunologic mechanism of caterpillars of *Galleria mellonella L;*

(2) the effect of the anti-antihemocytic serum on the intensification of growth of entomopathogenic bacteria *Bac.thuringiensis cereus var.galleriae* and *Bac.thuringiensis var. thuringiensis* which are constantly parasitizing in the organisms of caterpillars;

(3) the effect of the anti-antihemocytic serum on the immunity of caterpillars of *Galleria mellonella L* in combination with entomopathogenic bacteria *Bac.thuringiensis cereus var. galleriae.*

Tests of the action of the anti-antihemocytic serum on entomopathogenic bacteria *Bac. thuringiensis cereus var. galleriae* and *Bac. thuringiensis var. thuringiensis* were also carried out. The effect of the anti-antihemocytic serum on the immunologic mechanism of caterpillars and on the intensification of growth of entomopathogenic bacteria was checked every 6 hours from the beginning of the test.

The maximum intensity of the death rate of caterpillars of *G.mellonella L* was reached in 18 to 24 hours from the beginning of the test and made up 70 to 86% from the dose of 0.25 μl for every caterpillar and up to 100% from the dose of 2.50 μl. The test results are given in Table I.

Table 1

| Type of preparation | Doses of treatment for every caterpillar | Effectiveness of destruction of caterpillars, in % |
|---|---|---|
| 1. Anti-antihemocytic serum | 0.25 μl | 70 to 86 |
| | 2.50 μl | 100 |
| 2. Anti-antihemocytic serum in combination with entomopathogenic bacteria *Bac.thuringiensis cereus var.galleriae* | 0.25 μl 0.016 ml of a 0.1% water suspension of bacteria | 100 |

The tests for determining the action of the anti-antihemocytic serum on entomopathogenic bacteria *Bac.thuringiensis cereus var.galleriae* and *Bac.thuringiensis var.thuringiensis* showed that the anti-antihemocytic serum enhances the intensification of growth of said bacteria. The mechanism of this phenomenon resides not only in acquiring immune properties by insects but in the lowering of pathogenic possibilities of bacteria.

Example 2. Insects used are caterpillars of cabbage white butterfly *Pieris brassicae L.* The process of preparation of the anti-antihemocytic serum is identical with that described in Example 1.

The test of the anti-antihemocytic serum produced was carried out as in Example 1.

The dose of treatment of caterpillars of *Pieris brassicae L* with the anti-antihemocytic serum was 0.25 μl and 2.5 μl for every caterpillar. The effectiveness of destruction of caterpillars was 65% from the dose of 0.25 μl and 90% from the dose of 2.50 μl. When the anti-antihemocytic serum was used in a dose of 0.25 μl for every caterpillar in combination with entomopathogenic bacteria *Bac. thuringiensis cereus var.galleriae* in a dose of 0.016 ml of a 0.1% water suspension of bacteria for every caterpillar, the effectiveness of destruction of caterpillars was 100%.

What is claimed is:

1. Anti-antihemocytic serum comprising water-soluble proteins in a physiological solution isolated from cells of the bodies of insects immunized by a single injection in a dose of 0.25 μl to 2.0 μl for every insect with the anti-hemocytic serum produced from the plasma of the blood of an animal immunized with a suspension of hemocytes from cells of the body of the given species of insects; the titre of hemocytoagglutinins of the anti-antihemocytic serum is 1:256 to 1:1024.

2. A method for the preparation of anti-antihemocytic serum, residing in immunizing the given species of insects with anti-hemocytic serum, produced from the plasma of the blood of an animal immunized with a suspension of hemocytes from cells of the bodies of insects, by means of a single injection in a dose of 0.25 to 2.0 μl for every insect, removing the hemolymph and the alimentary tract from insects in 24 hours, homogenizing the remaining cells of the bodies of insects and diluting them with a physiological solution, isolating proteins from cells of the bodies of insects by breaking the integrity of cells, and isolating the fluid from the resultant mixture separating it from the indissoluble portion of cells of the bodies of insects, obtaining the target product.

* * * * *